United States Patent
Hardy et al.

(10) Patent No.: US 11,179,353 B1
(45) Date of Patent: Nov. 23, 2021

(54) COMPOSITION AND METHOD FOR PREVENTION AND TREATMENT OF RADIATION DERMATITIS

(71) Applicant: Rythera Therapeutics, Inc., Miami Lakes, FL (US)

(72) Inventors: Reginald L. Hardy, Ft. Lauderdale, FL (US); Mitchell Brigell, Belmont, MA (US)

( * ) Notice: Subject to any disclaimer, the term of this patent is extended or adjusted under 35 U.S.C. 154(b) by 0 days.

(21) Appl. No.: 17/028,746

(22) Filed: Sep. 22, 2020

(51) Int. Cl.
| | | |
|---|---|---|
| *A61K 31/137* | (2006.01) | |
| *A61K 31/135* | (2006.01) | |
| *A61K 9/00* | (2006.01) | |
| *A61K 31/07* | (2006.01) | |
| *A61P 17/02* | (2006.01) | |
| *A61K 31/59* | (2006.01) | |
| *A61K 31/355* | (2006.01) | |
| *A61K 45/06* | (2006.01) | |
| *A61K 31/375* | (2006.01) | |

(52) U.S. Cl.
CPC .......... *A61K 31/137* (2013.01); *A61K 9/0014* (2013.01); *A61K 9/0053* (2013.01); *A61K 31/07* (2013.01); *A61K 31/135* (2013.01); *A61K 31/355* (2013.01); *A61K 31/375* (2013.01); *A61K 31/59* (2013.01); *A61K 45/06* (2013.01); *A61P 17/02* (2018.01)

(58) Field of Classification Search
CPC .. A61K 31/137; A61K 9/0014; A61K 9/0053; A61K 31/07; A61K 31/135; A61K 31/355; A61K 31/375; A61K 31/59; A61K 45/06; A61P 17/02
See application file for complete search history.

(56) References Cited

U.S. PATENT DOCUMENTS

| | | | |
|---|---|---|---|
| 7,250,445 B1 | 7/2007 | Ehrenpreis | |
| 7,775,844 B2 | 8/2010 | St-Pierre et al. | |
| 2008/0233183 A1* | 9/2008 | McCook | A61K 47/186 424/450 |
| 2013/0079379 A1* | 3/2013 | Shanler | A61P 17/06 514/401 |
| 2015/0045403 A1* | 2/2015 | Shanler | A61K 45/06 514/400 |
| 2018/0140616 A1* | 5/2018 | Jow | A61K 31/38 |

FOREIGN PATENT DOCUMENTS

WO    WO-2016141219 A1 *    9/2016    ............. A61K 36/89

OTHER PUBLICATIONS

Shariati, Laleh, et al., Protective effects of doxepin cream on radiation dermatitis in breast cancer: A single arm double-blind randomized clinical trial. Br J Clin Pharmacol. 2020;86:1875-1881. https://doi.org/10.1111/bcp.14238.
Bray, F.N., et al., Acute and Chronic Cutaneous REactions to Ionizing Readiation Therapy, Dermatol. Ther. (2016) 6:185-206.
Uzuraga, I., et al., Topical amitriptyline, ketamine, and lidocaine in neuropathic pain caused by radiation skin reaction: a pilot study, Supppor Care Cancer (2012) 20:1515-1524.
Uiff, E., et al., Prophylactic treatment with a potent corticosteroid cream ameliorates radiodermatitis, independent of radiation schedule—A randomized double blinded study, Radiotherapy and Oncology, 122 (2017) 50-53.
Kole, A., et al., Acute radiation dermatitis in breast cancer patients: challenges and solutions, Breast Cancer—Targets and Therapy 2017:9 313-323.
Kornhuber, J., et al., Identification of Novel Functional Inhibitors of Acid Sphingomyelinase, PLoS ONE Aug. 2011, vol. 6, Issue 8, e23852.
Corre, I., et al., Membrane Signaling Induced by High Doses of Ionizing Radiation in the Endothelial Compartment. Relevance in Radiation Toxicity. Int. J. Mol. Sci. (2013), 14, 22678-22696.
Guo, Y.R., et al., The Neuroprotective Effect of Amitriptyline on Radiation-Induced Impairment of Hippocampal Neurogenesis, Dose Response an International Journal, Oct.-Dec. 2019:1-8.
Beckmann, N., et al., Inhibition of Acid Sphingomyelinase by tricyclic antidepressants and analogous, Frontiers in Physiology (2014) vol. 5, Art. 331, www.frontiersin.org, doi: 10.3389/fphys.2014.00331.
Leonetti, D, et al., Secretion f acid sphingomyelinase and ceramide by endothelial cells contributes to radiation-induced intestinal toxicity, (online) cancerres.aacrjournals.org, Apr. 14, 2020, DOI: 10.1158/0008-5472.CAN-19-1527.
American Association for Cancer Research (US), Leonetti, D, et al.. Secretion f acid sphingomyelinase and ceramide by endothelial cells contributes to radiation-induced intestinal toxicity, Apr. 14, 2020 (online publication) cancerres.aacrjournals.org. DOI: 10.1158/0008-5472.CAN-19-1527.

* cited by examiner

*Primary Examiner* — Robert A Wax
*Assistant Examiner* — Olga V. Tcherkasskaya
(74) *Attorney, Agent, or Firm* — Ted Whitlock Registered Patent Attorney, PA

(57) ABSTRACT

A composition comprising at least one TCA or SSRI useful in a method for preventing or treating a skin disorder such as radiation dermatitis, and method of preventing, ameliorating, or treating the skin disorder by administering an effective amount of the TCA, e.g., amitriptyline or the SSRI, e.g., sertraline.

7 Claims, No Drawings

COMPOSITION AND METHOD FOR PREVENTION AND TREATMENT OF RADIATION DERMATITIS

FIELD OF THE INVENTION

This invention is directed to compounds, compositions, and methods for preventing and treating a skin disorder, such as radiation dermatitis. More specifically, the invention relates to methods and compositions for preventing and treating radiation dermatitis using a tricyclic antidepressant (TCA), e.g., amitriptyline, or a selective serotonin reuptake inhibitor (SSRI), e.g., sertraline, in a topical dosage form. A composition of the invention can also include two or more active pharmaceutical ingredients formulated or mixed together in a single fixed-dose composition, such as a composition comprising two or more different TCA's, two or more different SSRI's, or one or more TCA in combination with one or more SSRI.

BACKGROUND OF THE INVENTION

Radiation therapy has traditionally been used for locally or regionally advanced cancer, and can be employed as a sole treatment or adjunctive to chemotherapy or surgery. Radiation may cause severe burns of the skin and surrounding tissue as well as permanent changes in pigmentation. As many as 95% of patients treated with radiation therapy for cancer will experience a skin reaction.

Aloe vera and topical Vitamin C have been tried without improvement in the results of irradiated breast tissue. Other reports indicate that the prophylactic and ongoing use of topical corticosteroid or a dexpanthenol-containing emollient can ameliorate, but not prevent, radiation dermatitis. Topical corticosteroids have little to no effect on pigmentation changes. Other reports have shown that moist skin care with 3% urea lotion delays the occurrence and reduces the grade of acute skin reactions in percutaneously irradiated patients with head and neck tumors.

Biafine and Lipiderm were shown to have no radioprotective effect, while significant dermato-cytoprotective effects were shown from the use of amifostine in a retrospective analysis.

Misoprostol, a prostaglandin E(1) analog, has been found to be an effective radioprotector in animal studies preventing oncogenic transformation of Syrian hamster embryos exposed to radiation in utero. However, successful results were not obtained in humans.

It has been proposed that damage to healthy tissue from radiation therapy may involve an endothelial response associated with signaling from the plasma membrane, via the acid sphingomyelinase/ceramide pathway (Corre, I., et al., Intl. J. Mol. Sci. (2013) 14, 22678-22696.) Protecting against endothelial damage, for example, by inhibiting acid sphingomyelinase (ASMase) activity, is suggested as a means for limiting radiation toxicity in normal tissues. Corre, supra, at 22685. Although inhibitors of ASMase are known, none have been developed for topical administration, nor demonstrated to be effective for prevention or treatment of radiation dermatitis The continued and increased use of radiation therapy in the treatment of cancer, and lack of available preventive or therapeutic medications for radiation dermatitis is a longstanding unmet patient need affecting millions of patients.

BRIEF DESCRIPTION OF THE INVENTION

The subject invention comprises a method for preventing, treating, ameliorating, or reversing radiation dermatitis comprising topically administering or applying a composition comprising at least one tricyclic antidepressant (TCA), at least one selective serotonin reuptake inhibitor (SSRI), or a combination thereof, and a pharmaceutically acceptable carrier. More specifically, the method of the invention comprises the steps of:

providing a topical composition comprising a pharmaceutically effective amount of at least one TCA or SSRI or combinations thereof.

topically administering or applying the composition to a patient in need thereof prior to radiation therapy or following radiation therapy or both.

It would be understood that applying the composition prior to radiation therapy can include retention of the composition at the location during the radiation therapy session. The method can be repeated for each radiation therapy session and can include administering or applying the composition at least one time per week, several times per week, daily, or multiple times daily, between radiation therapy sessions.

Alternatively, a method according to the subject invention can comprise orally administering a composition comprising an effective amount of at least one TCA or SSRI. Such oral composition can be an immediate release or controlled release dosage form.

A composition for use in a method of the invention can comprise between about 0.1-1000 milligrams (mg) of a TCA, such as amitriptyline, or an SSRI such as sertraline. A topical composition useful in accordance with a method of the invention can be provided as a topical liquid, but is preferably formulated as a topical cream, gel, lotion, or ointment. A preferred TCA useful as an active ingredient a composition and method of the invention is amitriptyline; a preferred SSRI useful as an active ingredient a composition and method of the invention is sertraline, but other compounds within the class of TCAs or SSRIs may be substituted or can be used in combination.

The topical dosage form can comprise a conventional base and a TCA or SSRI, and can further include other pharmaceutically acceptable excipients as conventionally employed in topical or oral dosage forms.

Preferably, the TCA or SSRI is provided in an immediate-release topical formulation which allows targeted dosing and immediate delivery of the drug from the composition to the skin upon application or administration of the composition.

An oral dosage form of a composition can be immediate-release or may be formulated with excipients, such as polymers, gels, waxes, or the like, incorporated into a matrix or comprising a coating to slow, delay, sustain, or extend release of the active ingredient from the composition following oral administration.

Tricyclic antidepressants useful in the method of the invention include one or more of: amineptine, amitriptyline, amoxapine, butriptyline, clomipramine, desipramine, dibenzepin, dosulepin, doxepin, imipramine, iprindole, lofepramine, maprotiline, norclomipramine, northiaden, nortriptyline, opipramol, protriptyline, tianeptine, or trimipramine. A preferred TCA is amitriptyline. According to a preferred embodiment, the dosage form of the invention comprises amitriptyline at a dosage of between 0.1-1000 mg; more preferably a dose of about 1 mg-100 mg, and most preferably a dose of about 5 mg-50 mg. It is contemplated that a preferred dose is about 10 mg of the TCA, formulated in a 1% (w/w) composition. The dose can vary, being lower in dosage forms that more rapidly deliver drug to the site, or higher in dosage forms that slowly release drug.

SSRIs useful in the method of the invention include one or more of: citalopram, escitalopram, fluoxetine, fluvoxamine, paroxetine, or sertraline. A preferred SSRI is sertraline. According to a preferred embodiment, the dosage form of the invention comprises amitriptyline at a dosage of between 0.1 mg-1000 mg; more preferably a dose of about 1 mg-100 mg, and most preferably a dose of about 5 mg-50 mg. It is contemplated that a preferred dose is about 10 mg of the SSRI, formulated in a 1% (w/w) composition. The dose can vary, being lower in dosage forms that more rapidly deliver drug to the site, or higher in dosage forms that slowly release drug.

According to a further aspect of the invention, the dosage form can include a second active TCA or SSRI ingredient, or can comprise a second active which is not a TCA or SSRI, for example, is an active ingredient in different class of drug. In a preferred embodiment, a composition comprises a first active ingredient which is a TCA or SSRI and a second active ingredient which is a different TCA or SSRI, or a second active ingredient which is not a TCA or SSRI, for example, an antioxidant, such as Vitamin A, Vitamin C, Vitamin D, and Vitamin E. Preferably, the second active in the composition is not an anti-inflammatory agent such as a non-steroidal anti-inflammatory drug (NSAID) nor an anesthetic agent, such as a local anesthetic, e.g., lidocaine.

Preferably, the method is carried out using a TCA or SSRI formulated in a topical composition which can deliver an effective dose to a target area of the skin which is directly or collaterally exposed to radiation during radiation therapy or treatment. For example, the active ingredient can be formulated as a liquid composition and administered as drops to the target area of the skin. Alternatively, the TCA can be formulated in a composition comprising a thickening agent or viscosity-enhancing agent as a lotion, cream, ointment or gel for topical delivery of the TCA to the target skin area of the patient. The topical formulation can be rubbed onto or into the target area of the skin prior to or following radiation therapy.

In the method employing a solid oral dosage form, the active ingredient can be provided as a particle, granule or bead and manufactured in the form of a tablet, capsule, caplet or the like, as would be readily understood in the art. The oral dosage form can be provided, for example, as a controlled release dosage form where the active ingredient is formulated in a delayed release dosage form, such as an enteric coated tablet, delayed release capsule or caplet, or can be formulated in a slow release matrix composition. Combinations of these controlled release dosage forms can also be employed.

Thus, in accordance with the invention, the method for preventing, treating, or ameliorating radiation dermatitis comprises topically administering to a target area of skin of a patient in need thereof at least one time per day prior to, during, and after radiation treatment, 0.5-5 ml of a composition comprising an effective amount of a TCA which is amitriptyline.

The method for preventing, treating, or ameliorating radiation dermatitis also comprises topically administering to a target area of skin of a patient in need thereof at least one time per day prior to, during, and after radiation treatment, 0.5-5 ml of a composition comprising an effective amount of a selective serotonin reuptake inhibitor which is sertraline.

The method also includes preventing, treating, or ameliorating radiation dermatitis, by topically administering to a target area of skin of a patient in need thereof at least one time per day prior to, during, and after radiation treatment, 0.5-5 ml of a composition comprising an effective amount of at least one active ingredient selected from a tricyclic antidepressant, a selective serotonin reuptake inhibitor, and a combination of a tricyclic antidepressant and a selective serotonin reuptake inhibitor.

A topical composition employed in the method can comprise 10 mg amitriptyline per ml of the composition or can comprise 10 mg sertraline per ml of the composition or can comprise 5-10 mg amitriptyline per ml of the composition and 5-10 mg sertraline per ml of the composition.

The above topical compositions can also include an antioxidant such as Vitamin A, Vitamin C, Vitamin D, and Vitamin E.

Preferably, the composition used in the method of the invention is formulated as a topical dosage form which delivers the effective dose of active ingredient in situ to the target area of the patient. This can be carried out using a composition formulated with a pharmaceutically acceptable base to form a lotion, cream, ointment, or gel for topical delivery of the active ingredient to a target area of skin of the patient.

Alternatively, the composition can comprise amitriptyline and a second tricyclic antidepressant which is not amitriptyline, such as amineptine, amitriptyline, amoxapine, butriptyline, clomipramine, desipramine, dibenzepin, dosulepin, doxepin, imipramine, iprindole, lofepramine, maprotiline, norclomipramine, northiaden, nortriptyline, opipramol, protriptyline, tianeptine, or trimipramine.

The composition comprising sertraline can comprise a second selective serotonin reuptake inhibitor which is not sertraline, such as citalopram, escitalopram, fluoxetine, fluvoxamine, or paroxetine.

The pharmaceutical composition of the invention can be provided as a topical pharmaceutical composition or can be an oral dosage form comprising an effective amount of the one or more active ingredient, such as amitriptyline, sertraline, or a combination thereof for delivery of the one or more active ingredients to the patient. In a preferred embodiment, a topical composition of the invention is free of, does not include, or excludes, an anti-inflammatory agent and an anesthetic agent.

A preferred topical pharmaceutical composition comprises 10 mg amitriptyline per ml of the composition, or 10 mg sertraline per ml of the composition, or 5-10 mg amitriptyline per ml of the composition and 5-10 mg sertraline per ml of the composition. Any of the above can further comprise an effective amount of an antioxidant such as Vitamin A, Vitamin C, Vitamin D, or Vitamin E.

An oral dosage form of the invention can be formulated as a controlled release oral dosage form.

It would be understood that the method and compositions and dosage forms of the invention can be useful for preventing, treating or ameliorating other dermal conditions such as atopic dermatitis, thermal burn, sunburn, dermatomyo-fibromas, exposure-induced wrinkles, or the like.

DETAILED DESCRIPTION OF THE INVENTION

The present invention provides an innovative method for preventing, ameliorating, or treating a skin condition in a mammal, including humans, and can employ the use of a novel composition or dosage form to carry out the method of treatment.

One embodiment of the invention relates to a method for preventing, ameliorating, or treating radiation dermatitis by administering an effective amount or dose of a TCA or SSRI.

Examples of TCAs useful in accordance with the subject invention are amineptine, amitriptyline, amoxapine, butriptyline, clomipramine, desipramine, dibenzepin, dosulepin, doxepin, imipramine, iprindole, lofepramine, maprotiline, norclomipramine, northiaden, nortriptyline, opipramol, protriptyline, tianeptine, and trimipramine. Examples of SSRIs useful in accordance with the subject invention are citalopram, escitalopram, fluoxetine, fluvoxamine, paroxetine, and sertraline, The invention includes the use of at least one TCA or SSRI and can include the use of at least two different TCAs, two different SSRIs or can include a TCA and an SSRI. Another embodiment of the invention includes the use of at least one TCA or SSRI, at least one TCA and at least one SSRI, and an additional active ingredient which is not a TCA or SSRI.

A preferred TCA for use in accordance with the subject invention is amitriptyline. Amitriptyline, marketed in the United States under the brand name ELAVIL® (AstraZeneca PLC, Cambridge England) is primarily used to treat a number of mental illnesses, including major depressive disorder, anxiety disorders, and less commonly attention deficit hyperactivity disorder (ADHD) and bipolar disorder. Other uses include prevention of migraines, treatment of neuropathic pain such as fibromyalgia and postherpetic neuralgia, and less commonly insomnia.

A preferred SSRI for use in accordance with the subject invention is sertraline. Sertraline, marketed in the United States under the brand name Zoloft® (Pfizer, New York, N.Y. USA) is primarily used to treat depression, panic attacks, obsessive compulsive disorder, post-traumatic stress disorder, social anxiety disorder (social phobia), and a severe form of premenstrual syndrome (premenstrual dysphoric disorder).

Amitriptyline and sertraline have not previously been known to be useful for prevention or treatment of radiation dermatitis.

In a preferred embodiment, at least one TCA or SSRI can be incorporated into a topical pharmaceutical composition for administration and placement onto the surface of the skin for the prevention, amelioration, or treatment of a dermal condition or disorder, such as radiation dermatitis. This treatment can be administered once daily, or more or less frequently as prescribed by the patient's physician or healthcare provider.

Topical compositions and dosage forms are well known in the art and are used conventionally in medical treatments. A preferred embodiment in accordance with the subject invention is to incorporate a TCA or SSRI active agent into a pharmaceutically compatible base composition to make a topical lotion, cream, gel, or ointment comprising the at least one TCA or at least one SSRI, as an active agent. Another embodiment of the invention includes incorporating two different TCAs, two different SSRIs, or a combination of at least one TCA and at least one SSRI as active agents into a pharmaceutically compatible base composition to make a topical lotion, cream, gel, or ointment. A preferred embodiment comprises the one or more active ingredients thoroughly mixed into a pharmaceutically acceptable base to provide a homogeneous mixture. For active ingredients that incompletely solubilize in the base, a suspension can be formed, wherein the suspension comprises an active ingredient which is thoroughly mixed to evenly disperse the active throughout the base. The composition of the invention can include other pharmaceutically acceptable excipients as conventionally employed in topical dosage forms.

In another embodiment of the invention, the active ingredient, such as one or more TCA or SSRI can be formulated for oral administration. In one embodiment, the oral dose is provided as an immediate release dosage form. In one embodiment, the oral dose is provided as controlled release dosage form.

Controlled release oral dosage forms include delayed release formulations created by coating a solid dosage form with a polymeric film, which is insoluble in the acidic environment of the stomach, and soluble in the neutral environment of the small intestine.

Composition of the invention may include conventional additives, such as plasticizers, pigments, colorants, stabilizing agents, glidants, etc.

"Radiation dermatitis" refers to a disorder of the skin resulting from radiation therapy of an area of the body underlying the skin. For example, radiation therapy is a known and accepted treatment for cancerous breast tissue in women and men. Inflammation of the skin covering the targeted cancerous tissue, and exposed to the radiation, can result in damage to the skin. These signs and symptoms are known as radiation dermatitis. The term is used herein as it is clinically understood by dermatologists and other physicians that treat such disorders.

The present invention provides a method for preventing, ameliorating, or treating radiation dermatitis by administration of a TCA or SSRI. The method includes a step of providing a composition comprising between about 0.001-10 grams of active ingredient and delivering the drug directly to the skin, either as a topical composition, such as a cream or lotion or ointment, or formulated in an oral dosage form.

According to a preferred embodiment, the TCA contained in the topical dosage form is amitriptyline at a dosage of between 1-1000 mg; more preferably a dose of about 5 mg-150 mg, and most preferably a dose of about 10-100 mg, where one preferred dosage is a suppository or other dosage form comprising about 10 mg, administered as a 1% w/w topical composition. For example, a composition comprising 1% active ingredient (10 mg of active ingredient per 1 ml of the composition) can be administered in amounts of about 0.5 ml to about 5 ml per topical application. Preferably, the composition is topically administered in about 1 ml to about 2 ml amounts to deliver 10-20 mg of the active ingredient to the skin for preventing or treating radiation dermatitis.

According to a preferred embodiment, the SSRI contained in the topical dosage form is sertraline at a dosage of between 1-1000 mg; more preferably a dose of about 5 mg-150 mg, and most preferably a dose of about 10-100 mg, where one preferred dosage is a suppository or other dosage form comprising about 10 mg., administered as a 1% w/w topical composition. The dose contained within the dosage form can vary, being lower in dosage forms that more rapidly deliver drug to the site, or higher in dosage forms that slowly release drug to the site.

The dose contained within the dosage form can vary, being lower in dosage forms that more rapidly deliver drug to the site, or higher in dosage forms that slowly release drug to the site. Dose variation can also depend on the active ingredient or ingredients contained within the composition. For example, a composition comprising a TCA and an SSRI can include each active at less than 1%, such as 0.1%-0.9%, preferably about 0.5% of each active, such that the final composition comprises 1% to less than 2% total active ingredient in the composition. This can advantageously lower the dose of each active ingredient being administered to the patient while providing an equivalent or substantially equivalent preventive or therapeutic effect. It is also contemplated that a fixed dose combination product comprising at least one TCA and at least one SSRI can provide a synergistic effect, wherein the efficacy is greater than the expected additive effect from the respective active ingredients used alone.

In one embodiment, the TCA or SSRI is provided in an oral dosage form as a controlled-release formulation which allows delivery of the drug over a period of time as compared to an immediate-release formulation which provides delivery of all the drug from the dosage form as soon as it is administered. Controlled release formulations known in the art include the use of coatings, such as enteric-coated tablets, beads, or pellets, ion exchange resins, waxes, alginates, gelling agents, such as cellulosic hydrogels (e.g., hydroxypropyl methyl cellulose, or HPMC) or polymeric acrylamides (e.g., CARBOPOL®) formulated with an active agent, and a suitable vehicle.

In a method according to the invention, treating, ameliorating, or preventing a skin disorder or condition such radiation dermatitis employs a composition comprising at least one TCA such as amitriptyline, and/or at least one SSRI such as sertraline. The composition employed in the method of the invention can be provided in a topical dosage form. In addition, the subject invention comprises a method for treating, ameliorating or preventing a skin disorder or condition such radiation dermatitis using an oral dosage form comprising at least one TCA such as amitriptyline, and/or at least one SSRI such as sertraline.

Preferably, the method comprises providing a topical dosage form comprising a composition having at least one TCA as an active ingredient, or having at least one SSRI as an active ingredient, or having a fixed dose combination of a TCA and SSRI as active ingredients, in a composition, and placing an effective amount of the composition onto a target area of skin to be treated, for that period of time required for delivery of the active ingredient to the site. In one preferred embodiment, the active ingredient or ingredients can be formulated as a viscous, controlled release gel, ointment, or cream for administration to the skin. A topical composition of the invention preferably comprises about 0.1% concentration (1 mg/ml of the composition) up to about 5% concentration (50 mg/ml of the composition) of each active ingredient provided; for example, 0.1%. 0.2%, 0.3%, 0.4%, 0.05%, 0.6%, 0.7%, 0.8%, 0.9%, 1.0% and 1.1%, 1.2%, 1.3%, and the like in 0.1% increments up to about 5.0%. A typical dose is about 0.5 ml to about 2 ml, preferably about 1 ml, but is not so limited, and is bounded only by the area of skin needed to be treated, such that a dose of 5 ml or greater can be applied.

According to one embodiment of the invention, the method of the invention comprises the step of:

topically administering an effective dose of one or more active ingredients, namely a drug in the class of TCAs or SSRIs, to the skin of a patient in need thereof, such as a patient who will undertake radiation therapy or who is suffering from radiation dermatitis.

Preferably, the method is carried out using amitriptyline as a TCA or sertraline as an SSRI, wherein the TCA or SSRI or both are formulated as a composition and provided in dosage form which is capable of delivering an effective dose in situ to the skin of the patient. For example, amitriptyline can be formulated as a liquid and administered in liquid form to the target area of the skin, or can be formulated with a thickening agent or viscosity-enhancing agent to provide a lotion, cream, ointment or gel for topical delivery of amitriptyline to target area of the skin of a patient in need thereof, such as a patient who will undertake radiation therapy or who is suffering from radiation dermatitis.

Alternatively, the method can employ administration of a solid oral dosage form.

The method of the invention can further include the administration to a patient in need thereof of at least one TCA or SSRI and an additional active ingredient which is not a TCA or SSRI. Preferably, the additional active is formulated together with the at least one TCA or SSRI in a fixed-dose combination drug product for topical administration to the skin.

One preferred embodiment of a composition of the invention having a first and second active comprises a TCA as a first active ingredient and an SSRI or an antioxidant as a second active ingredient. The antioxidant can be, for example, Vitamin A, Vitamin C, Vitamin D, and Vitamin E. A further embodiment of a composition of the invention can comprise a TCA, an SSRI, and an antioxidant. Examples of the active ingredients are amitriptyline as the TCA, sertraline, as the SSRI, and Vitamin A as the antioxidant.

Variable doses of the one or more active ingredient described herein may be utilized, depending on the condition being treated. For example, the topical dose of amitriptyline used for the prevention or treatment of radiation dermatitis is 1 mg-100 mg a day.

The optimal dosage and area to be treated to prevent or treat these conditions will be determined based on clinical studies. However, following appropriate clinical evaluation of this treatment, either larger or smaller doses of amitriptyline or sertraline may ultimately be used for preventing or treating radiation dermatitis as well as other dermatological inflammatory disorders.

EXAMPLES

Example 1—Use of a Composition Comprising a TCA

A patient undergoing or scheduled to undergo radiation therapy for treatment of a 25 mm breast tumor will be provided a composition which is an ointment comprising 1% amitriptyline in a pharmaceutically acceptable base. The area of the skin over the tumor, which is or will be exposed to the radiation during the radiation therapy procedure will be identified and can be marked. The healthcare worker or patient will administer the composition by applying approximately 1 ml of the composition to the area of the skin exposed or expected to be affected by the radiation at least one time per day before radiation treatment. Administration of the composition will be repeated at least daily, or up to five times daily following the radiation treatment for a period of one week.

Expected result: radiation dermatitis is prevented or ameliorated or reversed by the administration of the composition.

Example 2—Determining Efficacy of Single Active v a Plurality of Actives

Five patient groups undergoing or scheduled to undergo radiation therapy for treatment of a 25 mm breast tumor will be provided a composition which is an ointment comprising either:
  1% amitriptyline in a pharmaceutically acceptable base;
  1% sertraline in a pharmaceutically acceptable base;
  1% amitriptyline and 1% sertraline in a pharmaceutically acceptable base;

0.5% amitriptyline and 0.5% sertraline in a pharmaceutically acceptable base; and Pharmaceutically acceptable base, alone (placebo).

The area of the skin over the tumor, which is or will be exposed to the radiation during the radiation therapy procedure will be identified and can be marked. The healthcare worker or patient will administer the composition by applying approximately 1 ml of the composition to the area of the skin exposed or to be exposed to the radiation at least one time per day before radiation treatment. Administration of the composition will be repeated at least daily, or up to five times daily following the radiation treatment for a period of one week.

Expected results: The efficacy for each composition comprising an active ingredient will be determined by scoring the level of radiation dermatitis present in each group of patients. A determination of whether the efficacy of using amitriptyline and sertraline in combination exhibits an additive or synergistic effect can be determined by comparing whether the radiation dermatitis score for the composition comprising 1% amitriptyline and 1% sertraline is less than, equal to, or greater than the effect of the 1% amitriptyline composition, alone, and the 1% sertraline composition, alone. The radiation dermatitis score for the fixed dose combination composition comprising 0.5% amitriptyline and 0.5% sertraline in a pharmaceutically acceptable base can provide information on efficacy of lower doses of each active, in combination, compared to higher doses of each active, alone, in a composition.

The foregoing description of the invention is illustrative only and is not intended to limit the scope of the invention to the precise terms set forth. Further, although the invention has been described in detail with reference to certain illustrative embodiments, variations and modifications exist within the scope and spirit of the invention as described and defined in the following claims.

The invention claimed is:

1. A method for treating or ameliorating radiation dermatitis, wherein said method comprises topically administering to a target area of skin of a patient in need thereof at least one time per day prior to, during, and after radiation treatment 0.5-5 ml of a topical composition consisting of 5-50 mg/ml of sertraline and one or more pharmaceutically acceptable excipients.

2. The method of claim 1, wherein said sertraline is present in said topical composition in the amount of 4% w/w.

3. The method of claim 1, wherein the one or more pharmaceutical excipients include an antioxidant selected from the group consisting of vitamin A, vitamin C, vitamin D, and vitamin E.

4. The method of claim 1, wherein said topical composition is in a form of lotion, cream, ointment, or gel.

5. A topical sertraline composition for treating or ameliorating radiation dermatitis in a patient undergoing radiation therapy for treatment of cancer, wherein said composition consists of 5-50 mg/ml of sertraline and one or more pharmaceutically acceptable excipients, and wherein said sertraline composition is free of anti-inflammatory and anesthetic agents.

6. The topical sertraline composition of claim 5, wherein said sertraline is present in said composition in the amount of 4% w/w.

7. The topical sertraline composition of claim 5, wherein the one or more pharmaceutical excipients include an antioxidant selected from the group consisting of vitamin A, vitamin C, vitamin D, and vitamin E.

* * * * *